(12) United States Patent
Ouchi

(10) Patent No.: US 6,443,909 B1
(45) Date of Patent: Sep. 3, 2002

(54) BIOPSY FORCEPS FOR ENDOSCOPE

(75) Inventor: Teruo Ouchi, Saitama (JP)

(73) Assignee: Asahi Kogaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/479,064

(22) Filed: Jan. 7, 2000

(30) Foreign Application Priority Data

Feb. 9, 1999 (JP) ............................................. 11-031050

(51) Int. Cl.⁷ ................................................ A61B 10/00
(52) U.S. Cl. ..................................... 600/562; 606/205
(58) Field of Search ................................. 600/564, 565, 600/567–572, 566; 606/205, 206, 207, 208

(56) References Cited

U.S. PATENT DOCUMENTS

| 4,945,920 A | 8/1990 | Clossick |
| 6,015,381 A | 1/2000 | Ouchi |
| 6,024,708 A | * 2/2000 | Bales et al. ................. 600/564 |

FOREIGN PATENT DOCUMENTS

| DE | 19835445 | 3/1999 |
| GB | 232 1193 | 7/1998 |
| JP | 52-40616 | 9/1977 |
| JP | 61-18885 | 6/1986 |
| JP | 64-26017 | 2/1989 |
| JP | 10192286 | 7/1998 |
| JP | 11104071 | 4/1999 |

* cited by examiner

Primary Examiner—Kevin Shaver
Assistant Examiner—Pamela Wingood
(74) Attorney, Agent, or Firm—Greenblum & Bernstein, P.L.C.

(57) ABSTRACT

A biopsy forceps for an endoscope has a flexible sheath and a control wire axially movably inserted in the sheath. A control part is connected to the proximal end of the sheath. The control wire is advanced or retracted at the control part to open or close a pair of forceps cups pivotally provided at the distal end of the sheath. The sheath is formed from a member that does not twist in at least one direction about an axis thereof. A rotation control member is provided on or near the control part to rotate the sheath about the axis in a direction in which the sheath does not twist.

8 Claims, 5 Drawing Sheets

BIOPSY FORCEPS FOR ENDOSCOPE

BACKGROUND OF THE INVENTION

The present disclosure relates to subject matter contained in Japanese Patent Application No. 11-31050 (filed on Feb. 9, 1999), which is expressly incorporated herein by reference in its entirety.

1. Field of the Invention

The present invention relates to a biopsy forceps that is inserted into an instrument-inserting channel of an endoscope to take a piece of tissue for a biopsy specimen from a body cavity.

2. Description of the Prior Art

In general, a biopsy forceps used with an endoscope has a control wire axially movably inserted in a flexible sheath that is removably inserted into an instrument-inserting channel of an endoscope. The control wire is advanced or retracted at a control part connected to the proximal end of the sheath, thereby opening or closing a pair of forceps cups pivotally provided at the distal end of the sheath.

The forceps cups have cutting edges on their outer edges to cut off a small piece of tissue from the mucous membrane or the like in a body cavity. The cut piece of tissue is taken into the forceps cups as a biopsy specimen.

However, it is rare that a piece of tissue can be cut off from the mucous membrane or the like simply by closing the forceps cups. The actual practice is as follows. The forceps cups are closed to bite the mucous membrane, and in this state, a piece of tissue is taken from the mucous membrane in such a manner as to tear it off by pulling the control wire toward the proximal end of the sheath.

Consequently, not only the part of the mucous membrane bitten by the forceps cups but also the surrounding tissue may be damaged, resulting in an unnecessarily large wound. If there is a blood vessel in the part bitten by the forceps cups, the blood vessel may be torn off. This may cause profuse bleeding.

SUMMARY OF THE INVENTION

An object of the present invention is to provide a biopsy forceps for an endoscope which is designed to minimize the damage to the tissue around a part of the mucous membrane bitten by a pair of forceps cups, thereby reducing the bleeding from the part subjected to the bioptic operation.

Other objects and advantages of the present invention will become apparent from the following detailed description of illustrated embodiments of the invention.

According to the present invention, there is provided a biopsy forceps for an endoscope that includes a flexible sheath and a control wire axially movably inserted in the sheath. A control part is connected to the proximal end of the sheath. The control wire is advanced or retracted at the control part to open or close a pair of forceps cups pivotally provided at the distal end of the sheath. The sheath is formed from a member that does not twist in at least one direction about an axis thereof. A rotation control member is provided on or near the control part to rotate the sheath about the axis in a direction in which the sheath does not twist.

BRIEF DESCRIPTION OF THE DRAWINGS

The present invention may be more fully understood from the description of preferred embodiments of the invention set forth below, together with the accompanying drawings, in which.

DESCRIPTION OF THE EMBODIMENT

Embodiments of the present invention will be described below with reference to the accompanying drawings.

Figure 1:
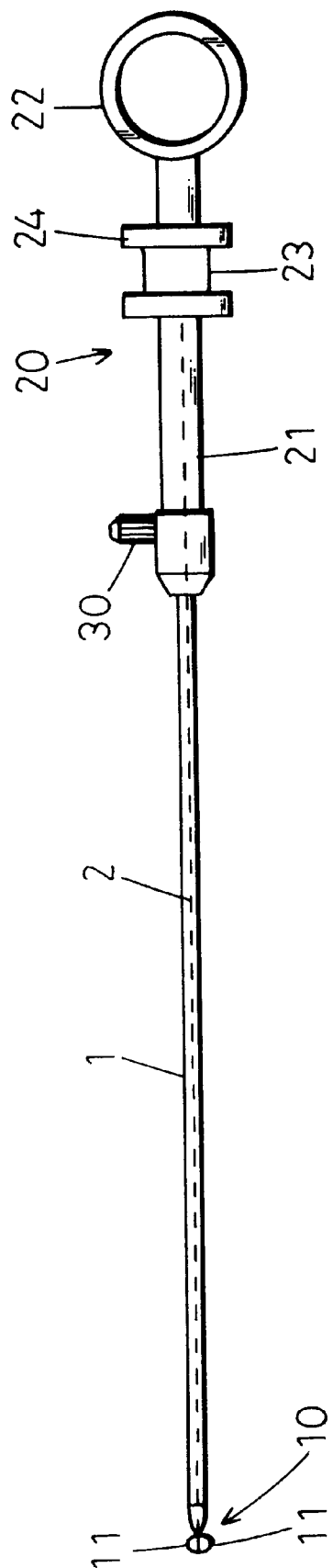
FIG. 1 is a side view of the whole arrangement of a biopsy forceps for an endoscope according to a first embodiment of the present invention.

FIG. 1 shows a biopsy forceps for an endoscope according to a first embodiment of the present invention. A flexible sheath 1 is removably inserted into an instrument guide tube (instrument-inserting channel) of an endoscope (not shown). A control wire 2 is axially movably inserted in the sheath 1 over the entire length thereof.

A control part 20 for advancing or retracting the control wire 2 is connected to the proximal end of the sheath 1. A distal end operating part 10 is connected to the distal end of the sheath 1. The distal end operating part 10 is driven by the control wire 2.

Figure 2:
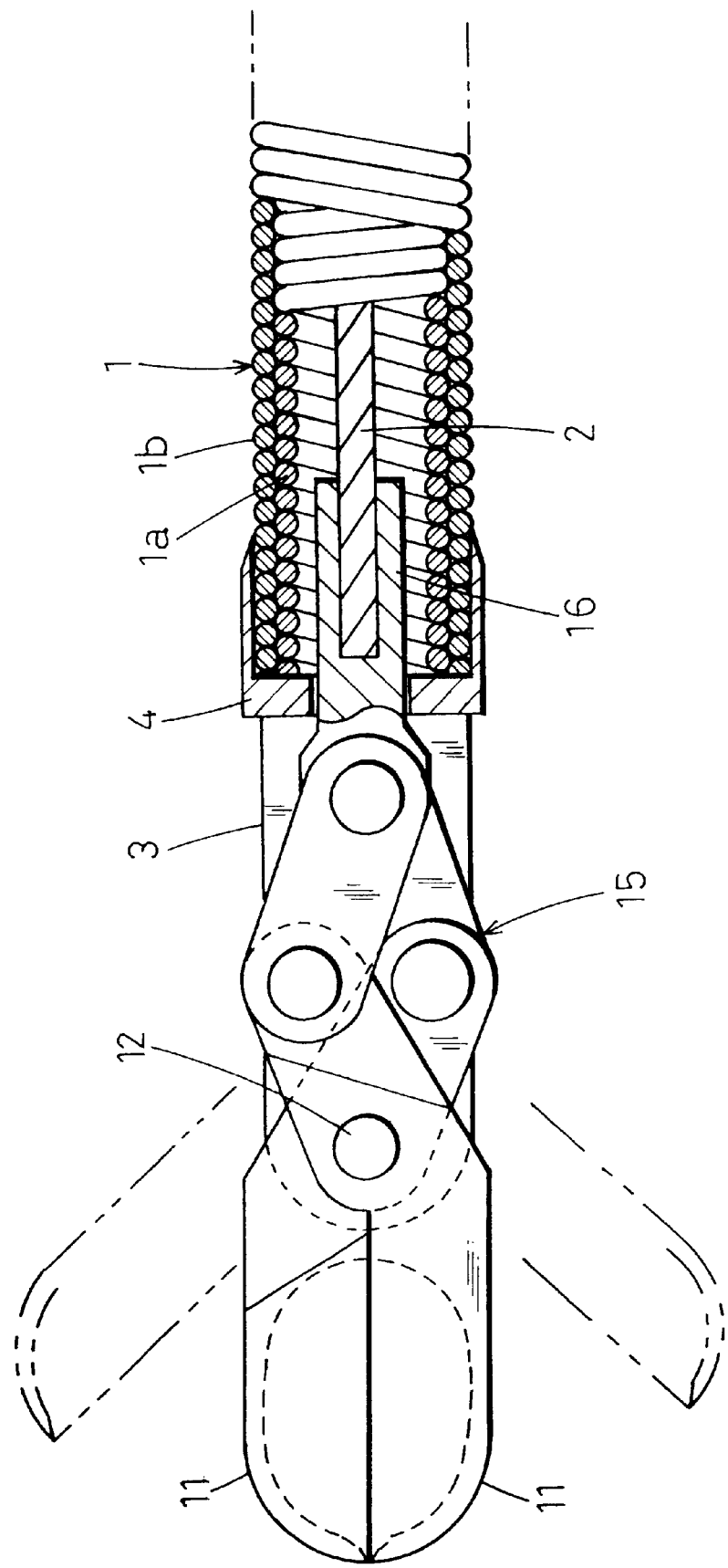
FIG. 2 is a sectional side view of a distal end portion of the biopsy forceps according to the first embodiment of the present invention.

FIG. 2 shows the distal end operating part 10. A distal end block 4 is firmly connected to the distal end of the sheath 1. The distal end block 4 has a large slit 3 cut from the forward end thereof. A pivot shaft 12 is mounted on the distal end block 4 in such a way as to cross the distal end portion of the slit 3.

A pair of forceps cups 11 are rotatably supported by the pivot shaft 12 so as to open or close in a beaklike manner about the pivot shaft 12. A publicly known link mechanism 15 is placed in the slit 3. The link mechanism 15 driven by the control wire 2 to open or close the forceps cups 11.

The link mechanism 15 has four links annularly connected together so as to be rotatable relative to each other in the form of a pantograph. Two forward links of the link mechanism 15 are integral and contiguous with the pair of forceps cups 11, respectively, and rotatable about the pivot shaft 12.

A driving rod 16 is connected to the rear end of the link mechanism 15. The distal end of the control wire 2 is firmly connected to the driving rod 16 to activate the link mechanism 15 by remote control from the proximal end of the sheath 1 (from the right-hand side as viewed in FIG. 2). When the control wire 2 is pushed toward the distal end of the sheath 1, the pair of forceps cups 11 open as shown by the chain double-dashed lines in FIG. 2. When the control wire 2 is pulled toward the proximal end of the sheath 1, the forceps cups 11 are closed as shown by the continuous lines in FIG. 2.

The sheath 1 is formed from two coil pipes 1a and 1b superimposed on one another with substantially no radial gap therebetween. The inner coil pipe 1a and the outer coil pipe 1b are each formed by close-winding a thin stainless steel wire, for example, with a uniform diameter. The winding direction of the inner coil pipe 1a and that of the outer,coil pipe 1b are opposite to each other:

Consequently, when the sheath 1 is rotated in a direction in which the inner coil pipe 1a is caused to expand radially, the outer coil pipe 1b is caused to contract radially. Therefore, the sheath 1 responds almost perfectly to rotation applied thereto in that direction. Accordingly, the sheath 1 can reliably transmit rotation without twisting between the two ends thereof.

If three or more coil pipes differing alternately in the winding direction are superimposed on one another without a gap to form a sheath 1, the sheath 1 exhibits almost perfect rotational response regardless of the direction of rotation.

The sheath 1 may be formed in a flexible pipe by using a shape-memory alloy, e.g. nickel-titanium alloy. In this case also, almost perfect rotational response can be obtained. Even when the sheath 1 is formed from a synthetic resin tube (e.g. a tetrafluoroethylene resin tube), fairly good rotational response can be obtained.

Figure 3:
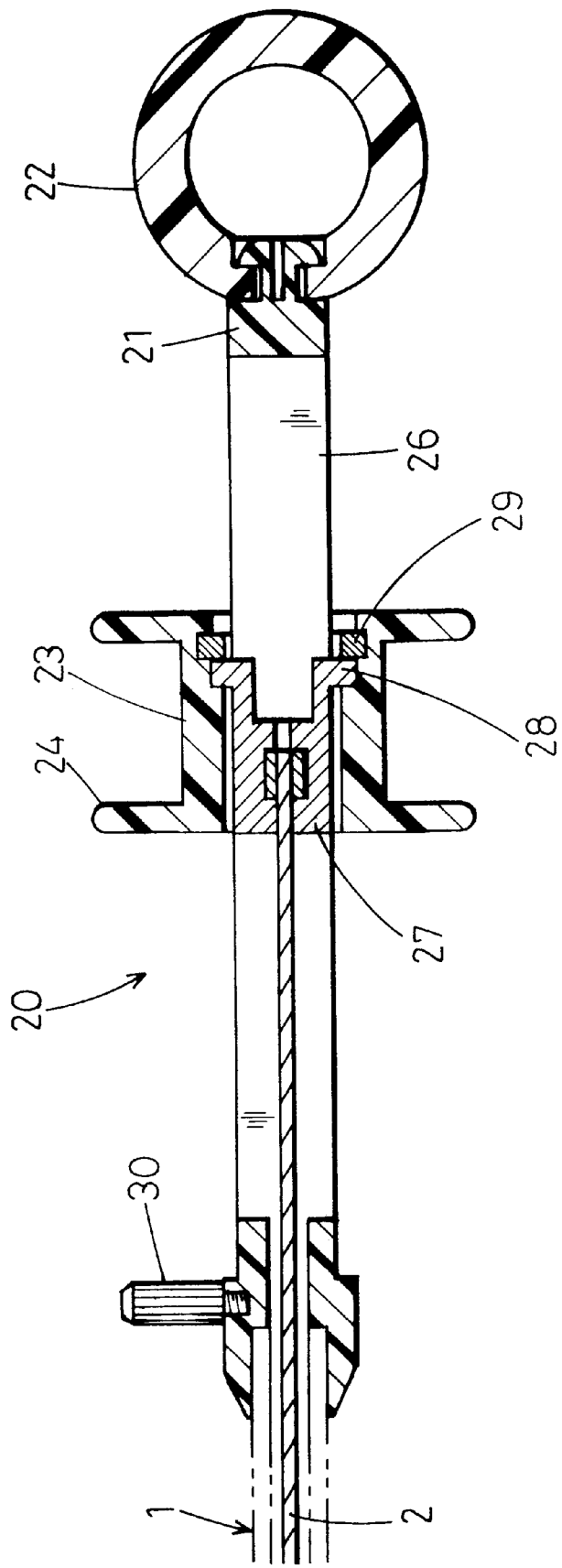
FIG. 3 is a sectional side view of a control part of the biopsy forceps according to the first embodiment of the present invention.

FIG. 3 shows the control part 20. The control part 20 has a control part body 21 formed in an elongate rod-like shape. A first finger engagement portion 22 for engagement with the operator's thumb is provided at the proximal end of the control part body 21 so as to be rotatable about the axis of the control part body 21. A slider 23 is provided on the control part body 21 so as to be slidable along the control part body 21 and rotatable about the axis thereof. The slider 23 is formed with a second finger engagement portion 24 for engagement with the operator's index and middle fingers.

An elongated slot 26 is formed in the control part body 21. A wire retainer 27 is positioned in the slot 26. The proximal end of the control wire 2 is secured to the wire retainer 27. A pair of engaging projections 28 formed on the wire retainer 27 are engaged with the inner surface of the slider 23.

A retaining ring 29 holds the engaging projections 28 to prevent them from disengaging from the slider 23. The wire retainer 27 and the slider 23 are engaged with each other so as to be rotatable relative to each other about the axis of the control part body 21 and movable in the axial direction as one unit.

The proximal end portion of the sheath 1 is coaxially secured to the distal end portion of the control part body 21. A rotation control pin 30 projects sideward from a side surface of the control part body 21 near the distal end thereof.

Accordingly, if the rotation control pin 30 is rotated about the axis of the control part body 21 with the operator's fingers engaged with the first and second finger engagement portions 22 and 24, the whole control part 20, exclusive of the first finger engagement portion 22 and the second finger engagement portion 24, rotates. In response to the rotation of the control part 20, the sheath 1 rotates about its own axis, and the rotation of the sheath 1 is transmitted to the distal end thereof as it is, causing the pair of forceps cups 11 to rotate about the axis of the sheath 1.

In operation with the biopsy forceps for an endoscope arranged as stated above, the control wire 2 is pulled to cause the pair of forceps cups 11 to bite the mucous membrane or the like, and in this state, the control part body 21 is rotated about its own axis by rotating the rotation control pin 30.

At that time, if the control part body 21 is rotated in a direction in which the inner coil pipe 1a of the sheath 1 is caused to expand radially, the pair of forceps cups 11 are driven to rotate about the axis of the sheath 1 in the state of biting the mucous membrane. Thus, a piece of tissue is cut off from the mucous membrane for a biopsy specimen. Consequently, it is possible to minimize the damage to the surrounding mucous membrane tissue and hence possible to reduce the bleeding from the part subjected to the bioptic operation.

Figure 4:
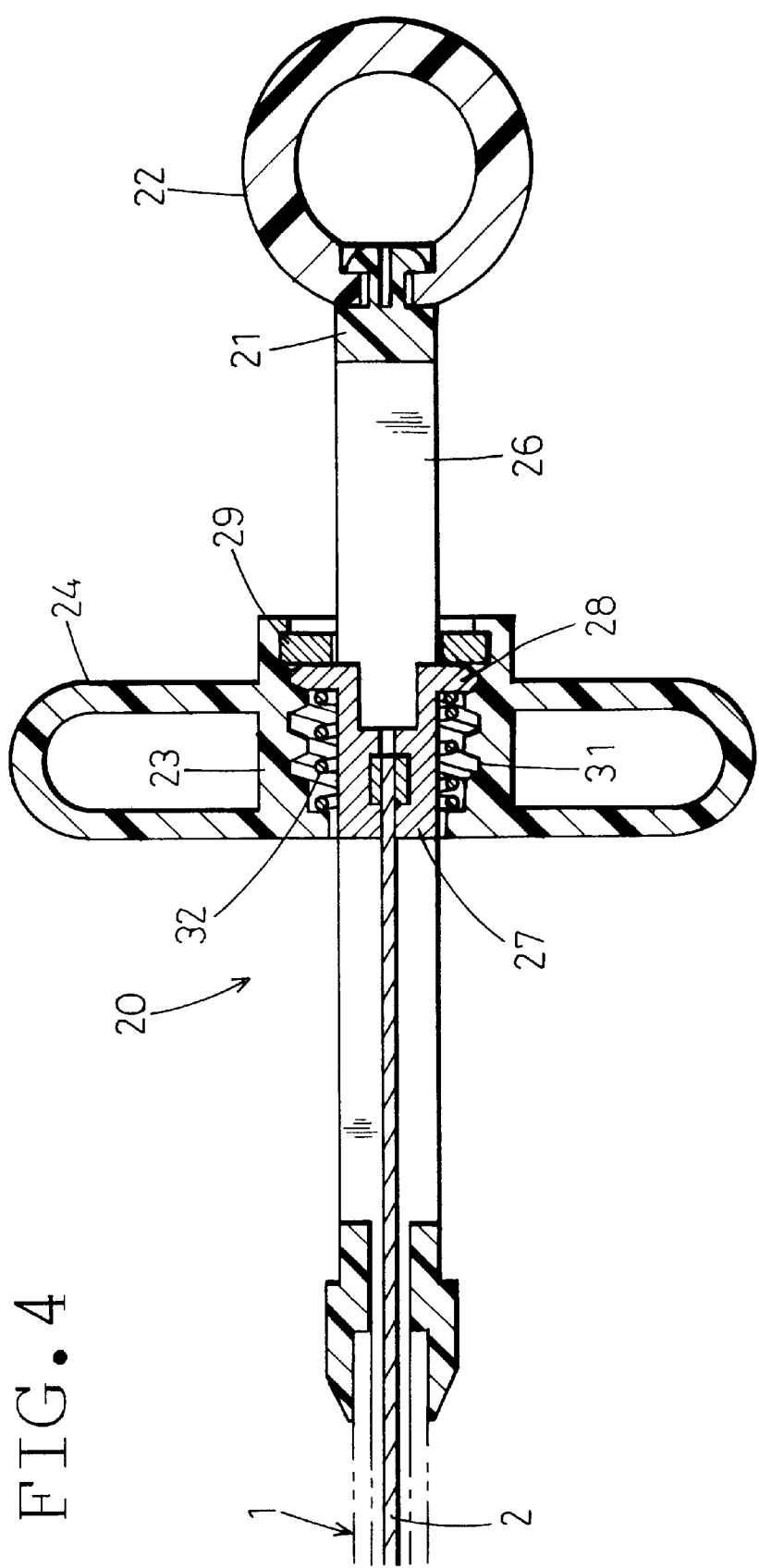
FIG. 4 is a sectional side view of a control part of a biopsy forceps for an endoscope according to a second embodiment of the present invention.

FIG. 4 shows a control part 20 in a second embodiment of the present invention, which is the same as the first embodiment in that the sheath 1 is firmly connected to the control part body 21, and the first finger engagement portion 22 and the second finger engagement portion 24 are provided so as to be rotatable relative to the control part body 21.

In the second embodiment, a pair of engaging projections 28 are formed on the wire retainer 27 in 180-degree symmetric relation to each other. The slider 23 is integrally formed with the second finger engagement portion 24. The engaging projections 28 and the slider 23 are in thread engagement with each other.

The slider 23 has a threaded portion 31 that uses a double thread having thread grooves cut in two rows. An axially compressed coil spring 32 is fitted to the threaded portion 31. A rotation control pin 30 or the like as provided on the control part body 21 in the first embodiment is not provided in the second embodiment.

In the second embodiment with the described arrangement, when the second finger engagement portion 24 is drawn toward the first finger engagement portion 22, first, the control wire 2 is pulled without causing the coil spring 32 to contract. Consequently, the pair of forceps cups 11 are closed to bite the mucous membrane.

When the second finger engagement portion 24 is further drawn toward the first finger engagement portion 22 with a stronger force, the engaging projections 28 and the slider 23, which are in thread engagement with each other, rotate relative to each other while contracting the coil spring 32. Consequently, the control part body 21 rotates about its own axis relative to the first finger engagement portion 22 and the second finger engagement portion 24, and the rotation of the control part body 21 is transmitted to the forceps cups 11 through the sheath 1 as in the case of the first embodiment. In this way, a piece of tissue for a biopsy specimen is taken from the mucous membrane.

Figure 5:
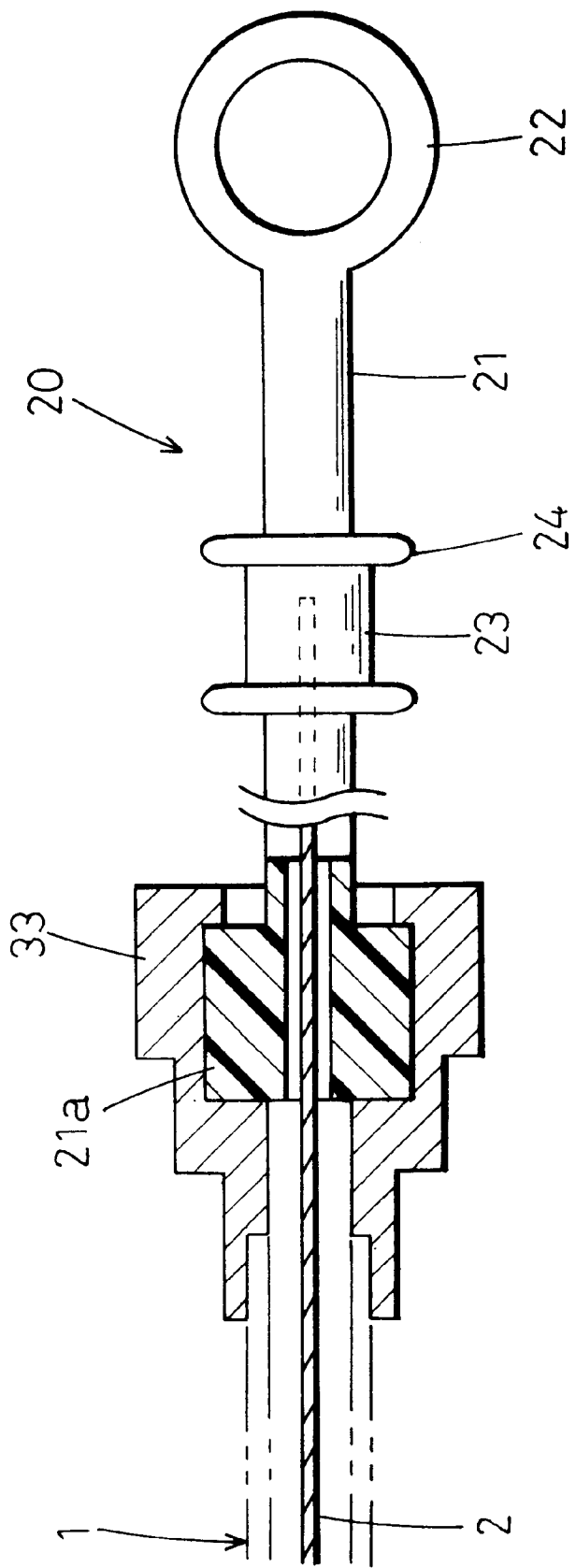
FIG. 5 is a partially-sectioned side view of a control part of a biopsy forceps for an endoscope according to a third embodiment of the present invention.

FIG. 5 shows a third embodiment of the present invention, in which a rotation control ring 33 secured to the proximal end of the sheath 1 is connected to a distal end portion 21a of the control part body 21 so as to be rotatable about the axis of the control part body 21. The first finger engagement portion 22 and the second finger engagement portion 24 need not be rotatable relative to the control part body 21.

By virtue of the above-described arrangement, rotating the rotation control ring 33 about the axis of the control part body 21 allows only the sheath 1 to rotate without causing the control part 20 to rotate, thereby rotating the forceps cups 11 at the distal end of the sheath 1. In this case, the sheath 1 and the control wire 2 may twist relative to each other. Therefore, it is desirable to use a stranded wire as the control wire 2.

According to the present invention, a piece of tissue for a biopsy specimen can be taken from the mucous membrane by rotating a pair of forceps cups through the sheath from the proximal end thereof in a state where the mucous membrane is bitten by the forceps cups. Therefore, it is possible to minimize the damage to the tissue around the part of the mucous membrane bitten by the forceps cups and hence possible to reduce the bleeding from the part subjected to the bioptic operation.

While the invention has been described by reference to specific embodiments chosen for purposes of illustration, it should be apparent that numerous modifications could be made thereto by those skilled in the art without departing from the basic concept and scope of the invention.

What is claimed is:

1. A biopsy forceps for an endoscope including a flexible sheath, a control wire axially movably inserted in the sheath, and a control part connected to a proximal end of the sheath, the control wire being advanced or retracted at the control part to open or close a pair of forceps cups pivotally provided at a distal end of said sheath, the biopsy forceps comprising:

said sheath comprising a material that is configured to not progressively twist in the longitudinal axial direction of said sheath; and a rotation control member provided in a vicinity of the control part to rotate said sheath relative to said control part about said longitudinal axial direction in which said sheath does not twist.

2. A biopsy forceps for an endoscope according to claim 1, wherein said sheath is formed from a plurality of close-wound coil pipes different in winding direction from each other, said close-wound coil pipes being superimposed on one another with substantially no radial gap therebetween.

3. A biopsy forceps for an endoscope according to claim 1, wherein said sheath is formed from a tubular member that is flexible and responsive to rotation.

4. A biopsy forceps for an endoscope according to claim 1, wherein finger engagement portions for engagement with operator's fingers are rotatably provided on said control part, and said sheath is connected to said control part so as to rotate about said longitudinal axial direction together with a portion of said control part other than said finger engagement portions as one unit.

5. A biopsy forceps for an endoscope according to claim 4, wherein said rotation control member is a projection provided on said control part so as to rotate the portion of said control part other than said finger engagement portions.

6. A biopsy forceps for an endoscope according to claim 4, wherein said finger engagement portions are a first finger engagement portion rotatably provided on said control part to allow engagement with a thumb of an operator's hand and a second finger engagement portion rotatably provided on said control part to allow engagement with index and middle fingers of said operator's hand, and said sheath is connected to said control part so as to rotate about said longitudinal axial direction together with a portion of said control part other than said first and second finger engagement portions as one unit.

7. A biopsy forceps for an endoscope according to claim 6, wherein said control wire is in thread engagement with said second finger engagement portion in a state where said control wire is urged with a spring, so that when said second finger engagement portion is drawn toward said first finger engagement portion, first, said control wire is pulled to close said forceps cups, and when said second finger engagement portion is further drawn toward said first finger engagement portion with a stronger force, the portion of said control part other than said first and second finger engagement portions is driven to rotate.

8. A biopsy forceps for an endoscope according to claim 1, wherein said sheath and said control part are connected together so as to be rotatable relative to each other about said longitudinal axial direction, and said rotation control member is connected to said sheath at a portion of said sheath where said sheath is rotatably connected to said control part so that said rotation control member rotates together with said sheath as one unit.

* * * * *